United States Patent [19]

Furukawa et al.

[11] Patent Number: 5,059,520
[45] Date of Patent: * Oct. 22, 1991

[54] MONOCLONAL ANTIBODY PANEL FOR BLOOD GROUP A ANTIGEN

[75] Inventors: Koichi Furukawa, New York, N.Y.; Hanrik Clausen; Sen-itiroh Hakomori, both of Seattle, Wash.; Junichi Sakamoto, Nagoya, Japan; Katherine Look, New York, N.Y.; M. Jules Mattes, Flushing, N.Y.; Lloyd Kenneth O., Bronx, N.Y.

[73] Assignee: Sloan-Kettering Institute for Cancer Research, New York, N.Y.

[ * ] Notice: The portion of the term of this patent subsequent to Apr. 6, 2006 has been disclaimed.

[21] Appl. No.: 900,820

[22] Filed: Aug. 27, 1986

[51] Int. Cl.$^5$ .................. G01N 33/53; G01N 33/577; C07K 15/14; C12N 1/00
[52] U.S. Cl. .............................. 435/7.21; 435/240.27; 435/7.23; 435/7.25; 436/503; 436/548; 436/811; 436/813; 530/387; 935/110; 424/11
[58] Field of Search ................ 436/548, 811, 813, 64, 436/501, 503, 518; 424/11, 85; 435/172.2, 68, 7, 240.27; 935/106, 110; 530/387

[56] References Cited

U.S. PATENT DOCUMENTS

| | | | |
|---|---|---|---|
| 4,579,827 | 4/1986 | Sakamoto et al. | 436/548 |
| 4,678,747 | 7/1987 | Lloyd et al. | 436/548 |
| 4,713,352 | 12/1987 | Bander et al. | 436/501 |
| 4,806,628 | 2/1989 | Albino et al. | 530/387 |

OTHER PUBLICATIONS

Furukawa et al., Biochemistry, vol. 24, Dec. 17, 1985, pp. 7820–7826.
Abe et al., Journal of Immunology, vol. 132, No. 4, 1984, pp. 1951–1954.
Veda et al., PNAS, vol. 76, 1981, pp. 5122–5126.
Clausen, PNAS, vol. 82, 1985, pp. 1199–1203.

*Primary Examiner*—Robert J. Warden
*Assistant Examiner*—Florina B. Hoffer
*Attorney, Agent, or Firm*—John P. White

[57] ABSTRACT

Monoconal antibodies HT29-36, CB, CLH6, M2, and S12 are useful in determining the presence of Type A blood group antigen and in distinguishing different forms of this antigen. As type A antigen exhibits several forms differing in minor respects only, the monoclonal antibodies are useful in making fine distinctions between the different forms, and may be used, e.g., in cancer diagnosis, and the like.

7 Claims, 22 Drawing Sheets

GLYCOLIPIDS a
A-1 a
A-2 a
A-3

H-3
1 a.
Gal-A b
A-2

GalNAcα1→3Galβ1→4GlcNAcβ1→3Galβ1→4Glcβ1→Cer
          2             3
          ↑             ↑                 y
     Fucα1    Fucα1           ALe

GalNAcα1→3Galβ1→3GlcNAcβ1→3Galβ1→4Glcβ1→Cer
          2             4
          ↑             ↑                 b
     Fucα1    Fucα1           ALe

GalNacα1→3Galβ1→3GalNAcβ1→3Galα1→4Galβ1→4Glcβ1→Cer
          2                               x
          ↑                          A (Globo-A)
     Fucα1

Galβ1→3GalNAcβ1→3Galα1→4Galβ1→4Glcβ1→Cer
 2
 ↑
Fucα1                                               Globo-H

OLIGOSACCHARIDES

A-HEPTA

A-HEXA

A-PENTA

A-TETRA

FIGURE 3 A

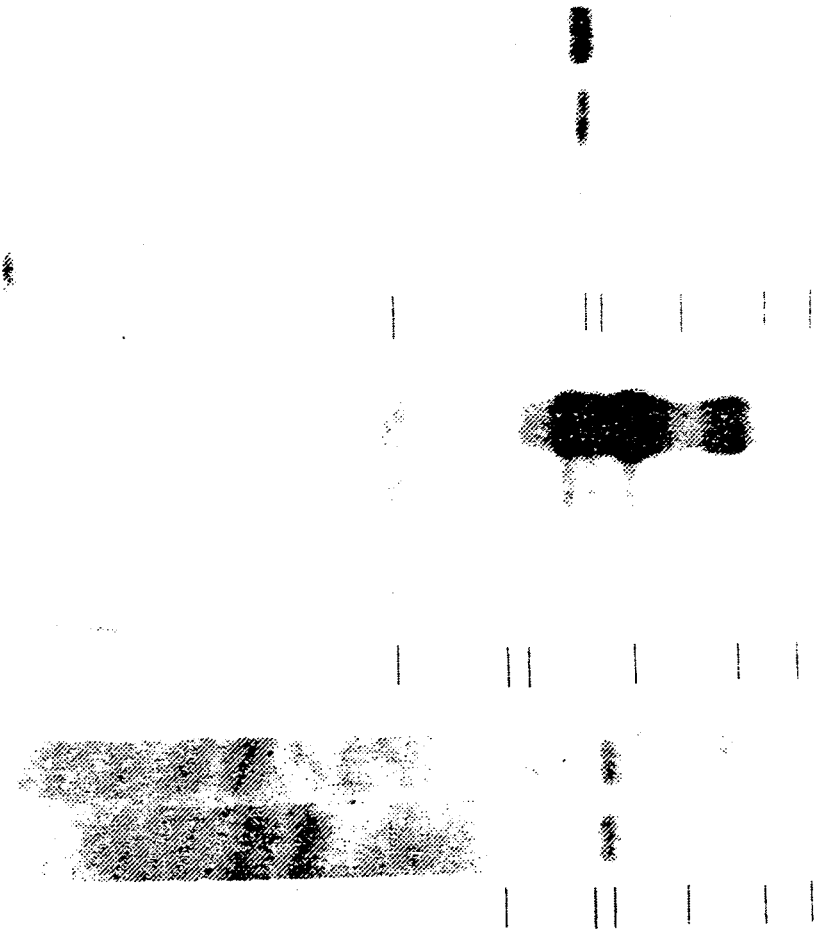

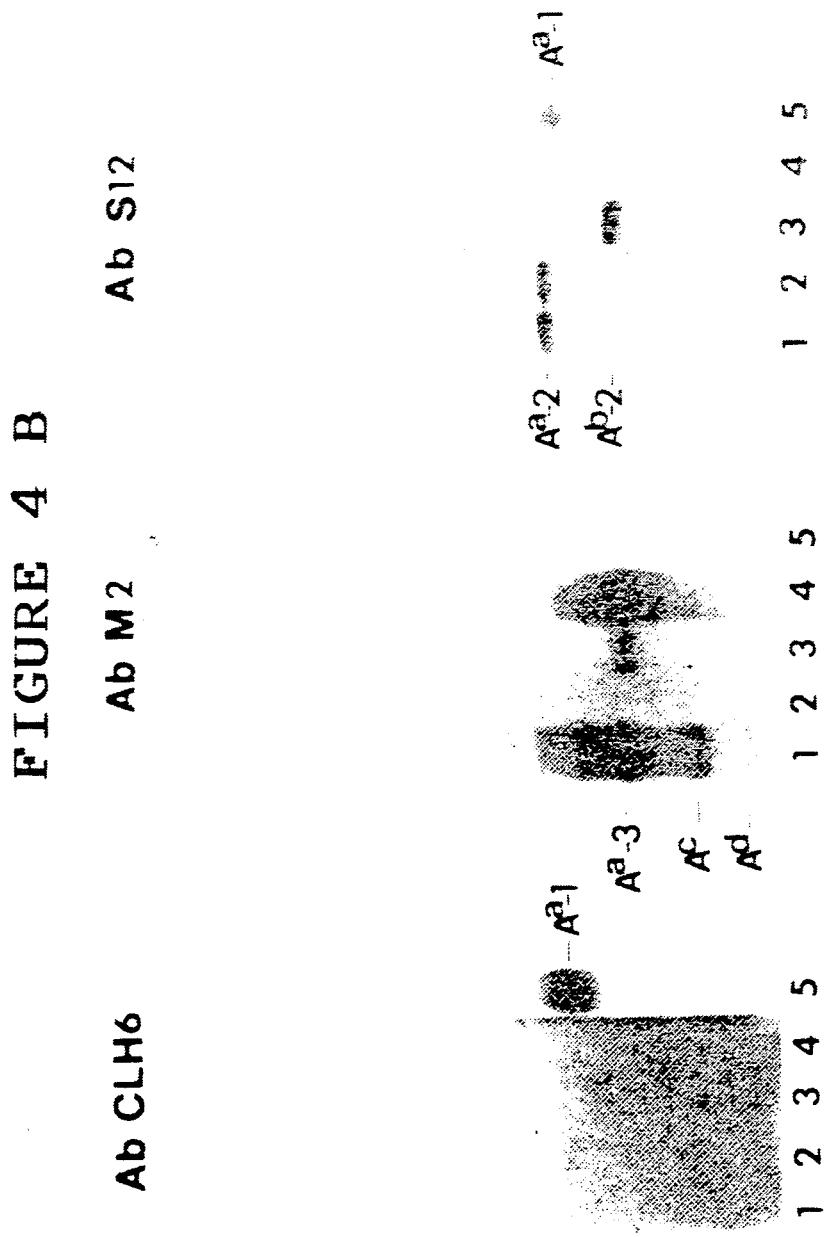

FIGURE 7 A

STRUCTURE REACTIVITY

H-3  Galβ1→3GalNAcα1→3Galβ1→R   ++
 1

Gal-A  Galβ1→3GalNAcα1→3Galβ1→R   +
                                  —

A-3  GalNAcα1→3Galβ1→3GalNAcα1→3Galβ1→R   +++

A (globo-A)    GalNAcα1→3Galβ1→3GalNAcβ1→3Galα1→R    +++
                         2
                         ↑
                        Fucα1

Globo-H     Galβ1→3GalNAcβ1→3Galα1→R    -
                    2
                    ↑
                 Fucα1

A - 2 (a)    GalNAcα1→3Galβ1→4GlcNAcβ1→Galβ1→R    -
                    2
                    ↑
                 Fucα1

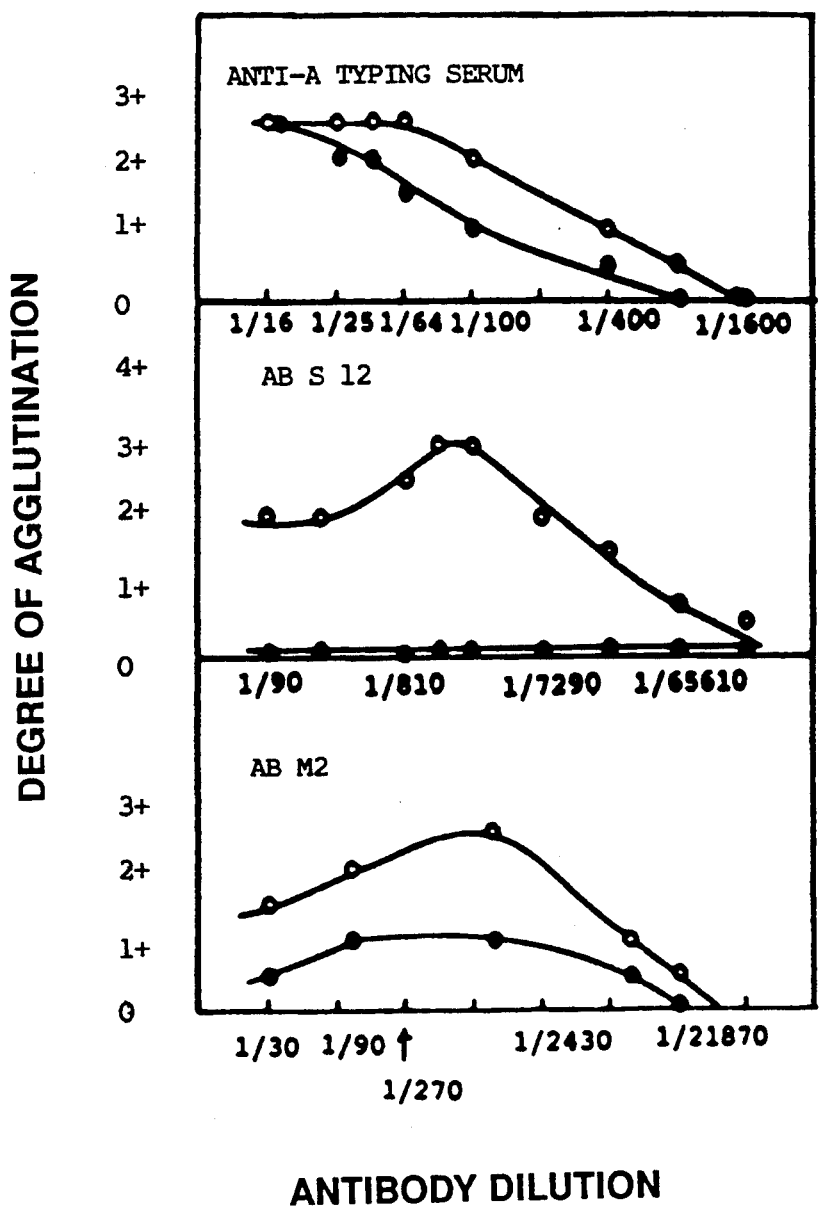

PRONASE TREATED R.B.C.

ANTIBODY DILUTION

AB CB VS. A  CELLS
1

AB CB VS. A₂ CELLS

AB S12 VS. A CELLS
2

AB S12 VS. A CELLS
1

MONOCLONAL ANTIBODY PANEL FOR BLOOD GROUP A ANTIGEN

The work for this application was supported in part by grants CA-34039, CA-08748, and CA-19224 from the National Cancer Institute. The U.S. Government has certain rights in this invention.

FIELD OF THE INVENTION

This invention relates to monoclonal antibodies useful in determining type A blood group antigen, and distinguishing the different forms of this antigen.

BACKGROUND AND PRIOR ART

The A, B, and O blood group antigens found on the surface of erythrocytes, are not confined to red cells but are found in most secretions and in many tissues of the human body. The immunodominant structure for the blood group A determinant, which is one of the most extensively studied specificities, is considered to be:

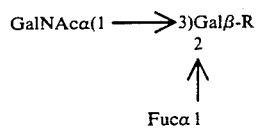

However, it has been found that the remainder of the carbohydrate chain (R) has much influence on the precise specificity of the determinant. Different blood group A variant structures have been described which have different sugars and sugar sequences in the R region. See, e.g., Kabat, *Carbohydrates In Solution*, pp. 334-361 (H. S. Isbell, ed.) (American Chem. Society, Washington, D.C.) (1973); Watkins, *Advances in Human Genetics*, (H. Harris & K. Hirschorn, ed.), v. 10, pp. 1-136 (1980); Hakomori, *Semin. Hematol.*, 18:39-62 (1981). For example, the A determinants (as well as the B, H. and Lewis determinants) are based on two different carbohydrate sequences, i.e., Galβ(1→3)GlcNAc (1→3)Galβ- or Galβ(1→4)GlcNAc (1→3)Galβ-. These structures, are designated type 1 and type 2 chains, respectively. More recently, a type 3 chain blood group determinant [extended or repetitive A: GalNacα(1→3)Galβ(1→3)GalNAcα(1→3)Galβ(1→4)GlcNAc] and a type 4 A chain based on the globo sequence [GalNAcα(1→3)Galβ(1→3)GalNAcβ(1→3)Galα(1→4)-Gal] have been described by Causen et al., *PNAS* 82:1199-1203 (1985); *Biochem Biophys Res. Commo.* 124:523-529 (1984). FIG. 1 illustrates various forms of the A antigen.

These human blood group antigens have traditionally been detected with allogeneic sera, which contains polyclonal antibodies with heterogeneous specificities. The technique for formation of hybridomas which produce monoclonal antibodies specific for particular antigens has made it possible, however, to conceive of the possibility of detecting blood group antigens using monoclonal antibodies, rather than allogeneic sera.

Voak et. al., *Vox Sang* 46:185-198 (1980), and Messetu, et. al., *Vox Sang* 46:185-198 (1984), have reported producing monoclonal antibodies to specific blood group antigens. Additionally, Barnstable, et. al., *Cell* 14:9-20 (1978); Edelman, et. al., *Immunol.* 44:549-555 (1981); and Abe, et. al., *J. Immunol.* 132:1951-1954 (1984), have all described monoclonal antibodies to the type A blood group antigens. For only a few of these, however, have specific antigenic determinants been recognized.

Recognition of different epitopes of the varieties of particular blood group antigens is now becoming recognized as important, however, because cells, cancer cells in particular, can express a variety of type A antigenic determinants on their surfaces which cannot be determined by conventional reagents. Determination of different antigenic determinants makes it possible to analyze the expression of A antigens, variants in normal and tumor samples, and allow one to search for alterations of expression in malignancy.

Hence, it is an object of this invention to provide a method of distinguishing between different types of type A blood group antigens, using monoclonal antibodies.

It is a further object of this invention to provide a panel of monoclonal antibodies which can be used to distinguish different type A blood group antigens.

The first object of the invention can be accomplished on any type of cell or tissue but is particularly useful in analysis and diagnosis involving cancer cells and tissues.

The monoclonal antibody panel of the invention may be used, as will be seen infra, to distinguish type A blood group antigens in extreme detail.

How the objects of this invention are accomplished will be seen from the disclosure which now follows.

BRIEF DESCRIPTION OF THE FIGURES

FIGS. 3A and 3B show immunostraining reactivity of monoclonal antibodies HT29-36 and CB with a neutral glycolipid extract of A and AB red blood cells.

FIGS. 4A and 4B compare antibodies HT29-36, CB, CLH 6, M2, and S12, with different forms of type A antigen.

DETAILED DESCRIPTION OF PREFERRED EMBODIMENTS

Hybridomas

The hybridomas described and claimed have been deposited with the American Type Culture Collection, 12301 Rockville, Md., and bear the following Accession Numbers:

| Hybridoma | ATCC Accession No. |
|---|---|
| HT29-36 | HB8248 |

| -continued |  |
|---|---|
| Hybridoma | ATCC Accession No. |
| M2 | HB8346 |
| S12 | HB8875 |
| CLH6 | HB8232 |

Further, the hybridomas have been deposited at the cell bank of the Sloan Kettering Institute for Cancer Research, 1275 York Avenue, New York, N.Y. 10021.

The origin and properties of these antibodies are summarized in the following Table 1. All were produced following the techniques of Köhler-Millstein.

Monoclonal antibody M2 was produced by immunization of mice with human renal cancer cell line SK-RC28. See, Ueda, et. al., *PNAS* 76:5122–26 (1981); U.S. patent application Ser. No. 297,814, filed Aug. 31, 1981. HT29-36 and CLH6 were produced by immunization with colonic cancer cell lines HT29, while S12 resulted from immunization with ovarian cancer cell line SK-OV-4. Ueda, supra; U.S. patent application Ser. No. 474,415, filed Mar. 11, 1983, now U.S. Pat. No. 4,579,827. CB is a commercial anti-A typing serum, and *Dolichos biflorus* lectin (*D. biflorus* is standard anti-$A_1$ lectin.

Glycolipids

Figure 1:
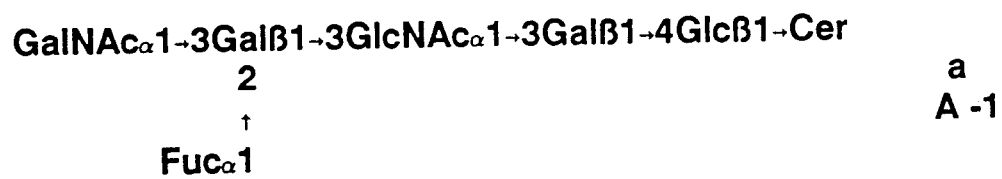
FIGS. 1A-1E show the glycolipid and oligosaccharide structures of different blood group antigens.
Figure 1:
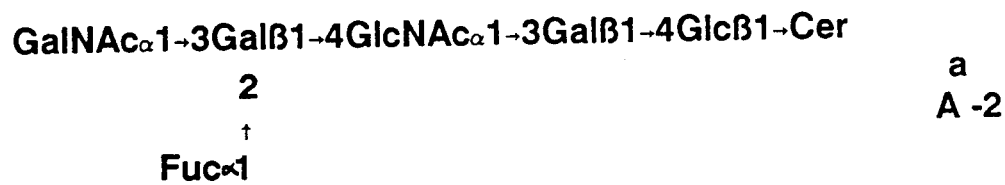
Figure 1:
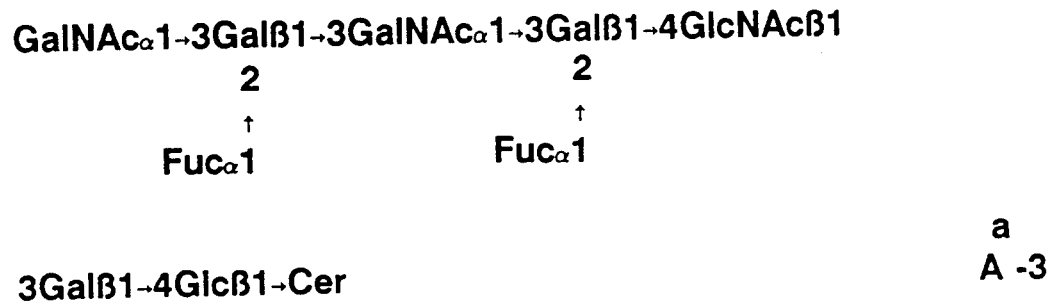
Figure 1:
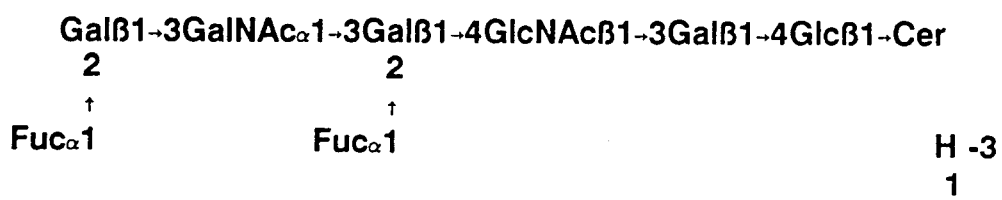
Figure 1:
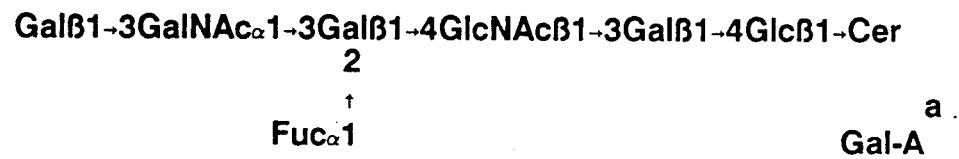
Figure 1:
Figure 1:
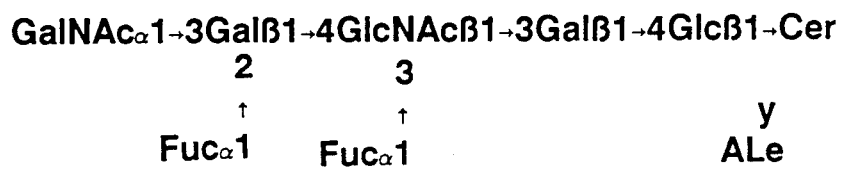
Figure 1:
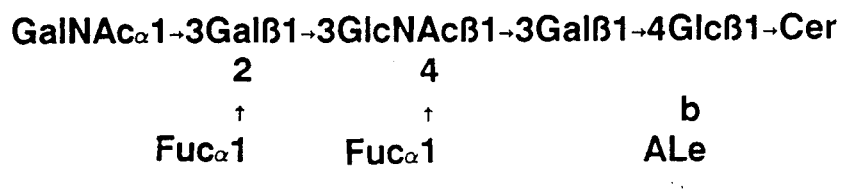
Figure 1:
Figure 1:
Figure 1:
Figure 1:
Figure 1:
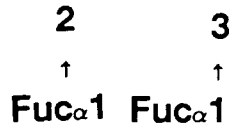
Figure 1:
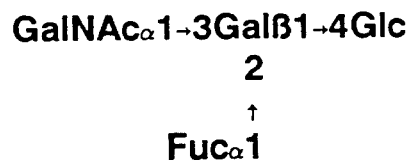

The structures of the blood group A active glycolipids and few of their precursor derivatives used in this study are shown in FIG. 1. Type1$A^a$ ($A^a-1$) was isolated from human gastric cancer cell line MKN45 as described by Abe, et. al. *J. Immunol* 132:1951–1954 (1984). Type 2 $A^a$ ($A^a-2$) and type 2 $A^b$ ($A^b-2$) were extracted from human A erythrocytes and were purified and identified as described by Hakomori et al. Type 3 A ($A^a-3$) and $A^x$ (Type 4 chain A, or globo-A) are recently described human red cell glycolipids. See, e.g., Clausen, et. al., *PNAS* 82:1198–1203 (1985); *Biochem. Biophys. Res. Commun.* 124:523–529 (1984). Type 3 chain ($H_1-3$) and -galactosyl A were prepared according to the method to be described elsewhere (Clausen, H., Levery, S. B., and Hakomori, S., unpublished results).

Ceramide trihexoside, globoside, GM1, GD1a, and GT used were obtained from commercial suppliers. Other gangliosides were isolated from human melanoma cells as described previously by Pukel, et. al., *J. Exp. Med.* 155:1133–1147 (1982). Lacto-N-tetraosyl- and lacto-N-neotetraosyl ceramide and $Le^a$, $Le^b$, H-1, H-2, X, and Y-active glycolipids have been described by McKibbin, et. al., *J. Biol. Chem.* 257:755–760 (1982); Lloyd, et. al., *Immunogen* 17:537–541 (1983). Forssman antigen (GalNAc$\alpha(1\rightarrow3)$GalNAc$\alpha(1\rightarrow3)$Gal$\beta(1\rightarrow4)$Gal$\beta(1\rightarrow4)$Glc - Cer was also used.

Glycoproteins and oligosaccharides

Human A(MSS 10%, Sullivan), B(Beach, phenol insoluble), HLe$^b$ (Tighe, phenol insoluble), Le$^a$ (N-1, 10% of 20%) and precursor (OG, 10% of 20%) ovarian cyst fluid glycoproteins and hog gastric mucin have been described by Lloyd and Kabat, *PNAS* 61:1470–77 (1968). Salivary glycoproteins were prepared from saliva by Pronase digestion as described by Sakamoto, et. al., *Mol. Immunol.* 21:1093–1098 (1984). Oligosaccharides (A-tetra, A-penta, A-hexa, and A-hepta; FIG. 1) were isolated from feces of a breast-fed infant as described by Sabharwal, et. al., *Mol. Immunol.* 21:1105–1112 (1980).

Extraction and Isolation of Glycolipids from Erythrocytes

For the isolation of total neutral glycolipids from A, B and O erythrocytes, out-dated blood was obtained from the Blood Bank of Memorial Sloan-Kettering Cancer Center. These blood samples were washed twice with ACD solution and membranes were prepared by hypotonic shock in 7 mM phosphate buffer, pH 7.2. The membrane preparation was lyophilized and extracted sequentially in 30 volumes of chloroform/methanol 2:1, 1:1 and 1:2. A glycolipid fraction was subsequently isolated by Florosil chromatography of the acetylated samples as described by Saito and Hakomori, *J. Lipid Res.* 12:257–259 (1971). After deacetylation and desalting, a neutral glycolipid fraction was obtained by DEAE-Sephadex(A50) chromatography as described by Yu and Ledeen, *J. Lipid Res.* 13:680–686 (1972).

Hemagglutination Assays

Hemagglutination assays were performed by both macroscopic and microscopic methods. For the macroscopic methods 25 ul of a 1% suspension of erythrocytes in PBS was added to 25 ul of serially diluted antibody in 96 well U-bottom plates. The results were read visually after incubation at 4° C. for 2 hr. For the microscopic method, 10 ul of 0.1% erythrocyte suspension was added to 10 ul of serially diluted antibody in 60 well HLA plates. After shaking gently, the plates were incubated at 4° C. overnight and examined under a microscope. Agglutination was scored as 4+, 3+, 2+, 1+, or − according to the degree of clumping.

Immunostaining Procedure

The reactivity of antibodies with glycolipids after separation by thin layer chromatography was performed according to the method of Magnani, et. al., *Anal. Biochem.* 109:399–402 (1980), with some modification as described by Young, et. al., *J. Biol. Chem.* 758:4890–94 (1983). In brief, the glycolipids were fractionated on aluminum-backed silica gel F254 sheets in chloroform:methanol:water (60:35:8). After drying the sheets were dipped for 1 min. in n-hexane saturated with polyisobutylmethacrylate and then sprayed with PBS containing 2% bovine serum albumin and 0.1% Na $N_3$, pH 7.3 (Solution A). After immersing them in Solution A for 2-3 hrs., monoclonal antibody solutions were layered on the sheets and incubated for 3 hr. After washing 5 times with PBS, rabbit anti-mouse IgG was added and incubated for 1.5 hr. After washing, $^{125}I$-labelled protein A in Solution A was added and incubated for 1 hr. After washing and drying, the sheet was exposed to X-Omat AR film for 15-24 hrs.

Solid Phase Binding and Inhibition Assays

The reactivity of antibodies with salivary and ovarian cyst glycopriteins was examined by ELISA according to the procedure previously described by Sakamoto, et. al., supra. In brief, glycoprotein samples, dissolved in water, were added to the wells of HLA plates, air dried overnight and then in vacuo over $P_2O_5$ for 1 hr. The plates were then preincubated with PBS containing 0.1% BSA for 2 hr. Ten ul of antibody was then added and incubated for 45 min. at room temperature. After washing 5 times with PBS, 10 ul of goat anti-mouse IgG (whole IgG) conjugated with alkaline phosphatase was added at 1:200 dilution. After incubation for 45 min. and washing, 10 ul of p-nitrophenyl phosphate was added.

After incubating at 37° for 15-30 min., the absorbance was read in an ELISA reader at 405 nm. Inhibition assays were performed by mixing oligosaccharides with an appropriate dilution of the antibody and testing residual antibody reactivity with the ELISA assay using 8 ng of A glycoprotein/well (or neutral A glycolipids, in the case of M2).

ELISA was performed on glycolipids according to the same procedure, except that methanol was used for dilution of the glycolipids and they were dried for 1 hr. at room temperature as described by Lloyd, et. al., supra. Solid phase radioimmunoassays were performed as described previously by Kannagi, et. al., Cancer Res. 43:4997-5005 (1983).

RESULTS

Reactivity of Monoclonal Antibodies with Erythrocytes

The ability of the 5 monoclonal antibodies to agglutinate A, B, AB, and O erythrocytes is shown in Table I. Antibodies CB, HT29-36 and M2 erythrocytes from all A and AB individuals. Antibody M2 reacted strongly with red cells from some individuals but weakly with those from other individuals. Antibody S12 agglutinated only about 80% of the A and AB samples tested. Antibody CLH6 did not agglutinate any of the erythrocyte samples tested. None of the 5 monoclonal antibodies agglutinated B or O red cells or sheep red cells.

Reactivity of Monoclonal Antibodies with Glycoproteins

The five monoclonal antibodies were examined for their reactivity with glycoproteins from human ovarian cyst fluids and hog gastric mucin using an ELISA assay. As shown in Table II, all antibodies reacted with MSS and Sullivan A substances except that M2 gave a weaker reaction. HT29-36 and CB showed strong reactivity with hog A and H mucin, S12 and CLH6 showed intermediate reactivity, and M2 was unreactive. None of the antibodies showed significant reactivity with B, HLe$^b$, or Le$^a$ glycoproteins.

Figure 2:
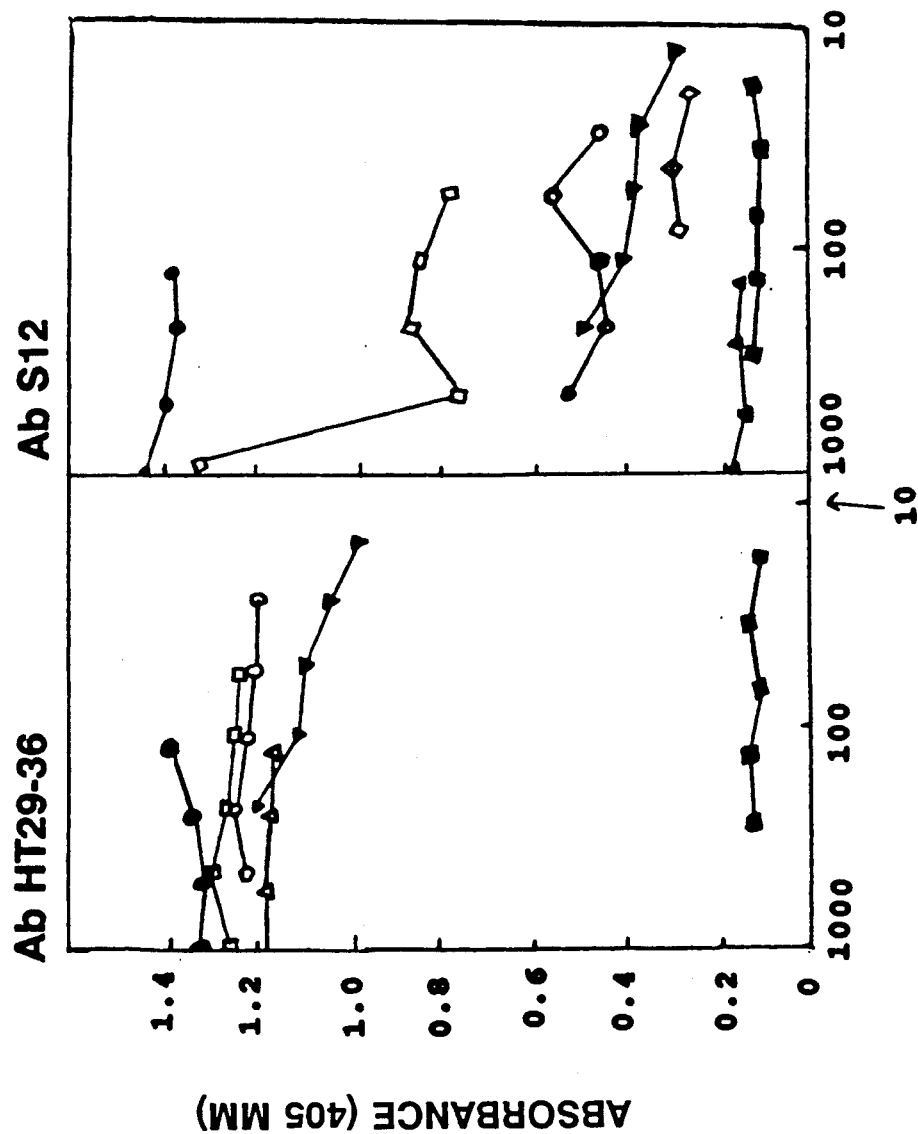
FIG. 2 shows reactivity of monoclonal antibodies S12 and HT29-36 with salivas from different individuals.

The reactivity of the antibodies to partially purified salivary glycoproteins from 33 individuals was also tested (Table I). HT29-36, CB and CLH6 reacted with all A and AB salivas from secretor individuals, except that CLH6 did not react with one sample of A$_2$ type saliva. M2 showed no reaction with any of the saliva samples tested. S12 reacted weakly with saliva from ⅓ of the A$_1$ and A$_1$B individuals; none of the salivas were as reactive as ovarian cyst glycoproteins (FIG. 2).

Reactivity of Antibodies with Erythrocyte Total Neutral Glyco Lipids and Purified A Glycolipids by Immunostaining of Thin Layer Chromatograms.

Figure 3A:
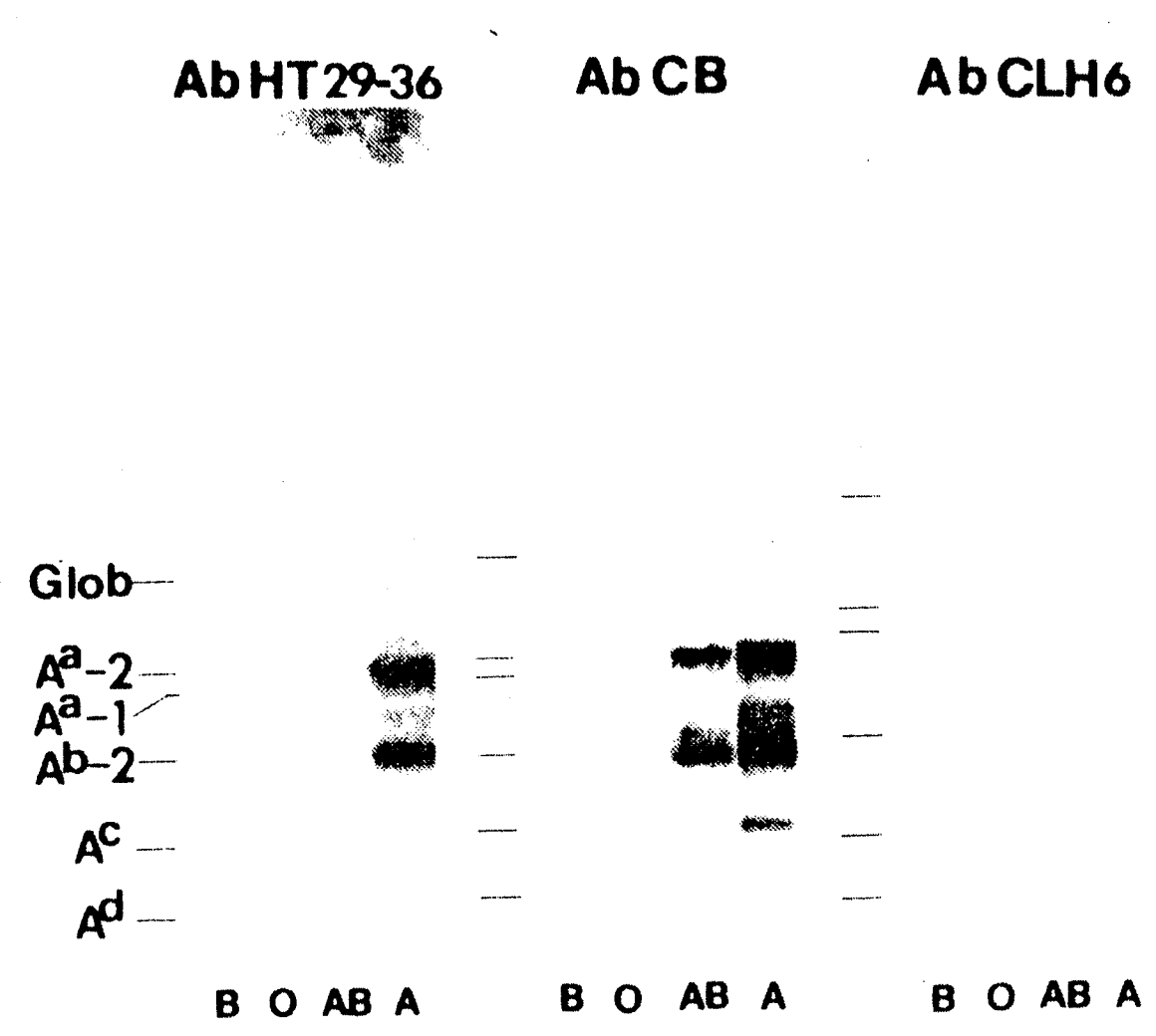
Figure 4A:
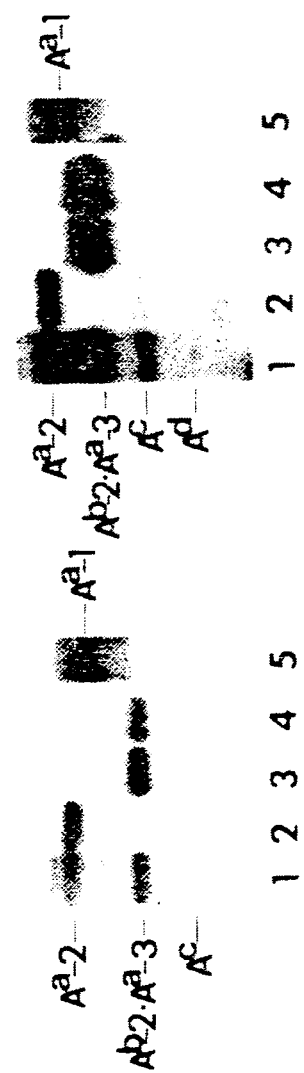
Figure 5:
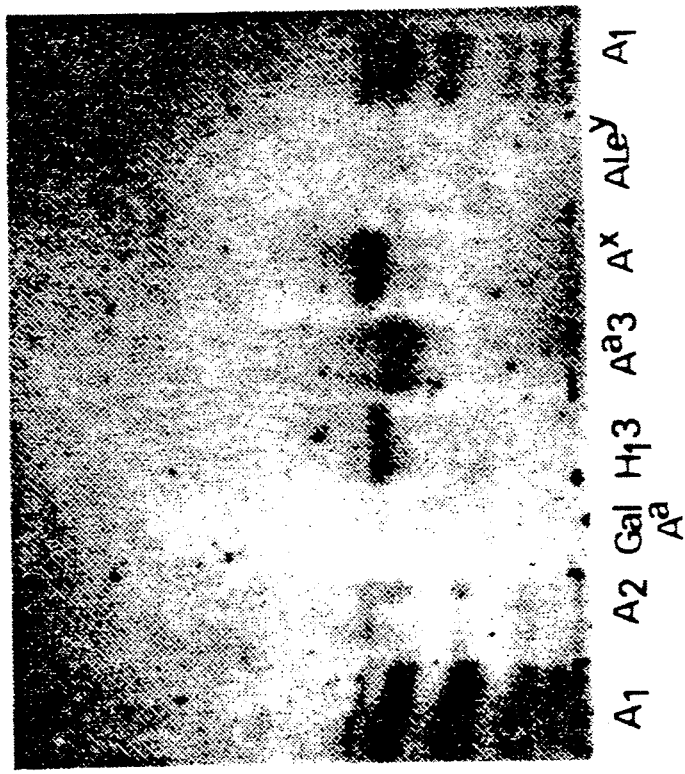
FIG. 5 shows reactivity of antibody M2 with various blood group antigens, using immunostaining.
Figure 6:
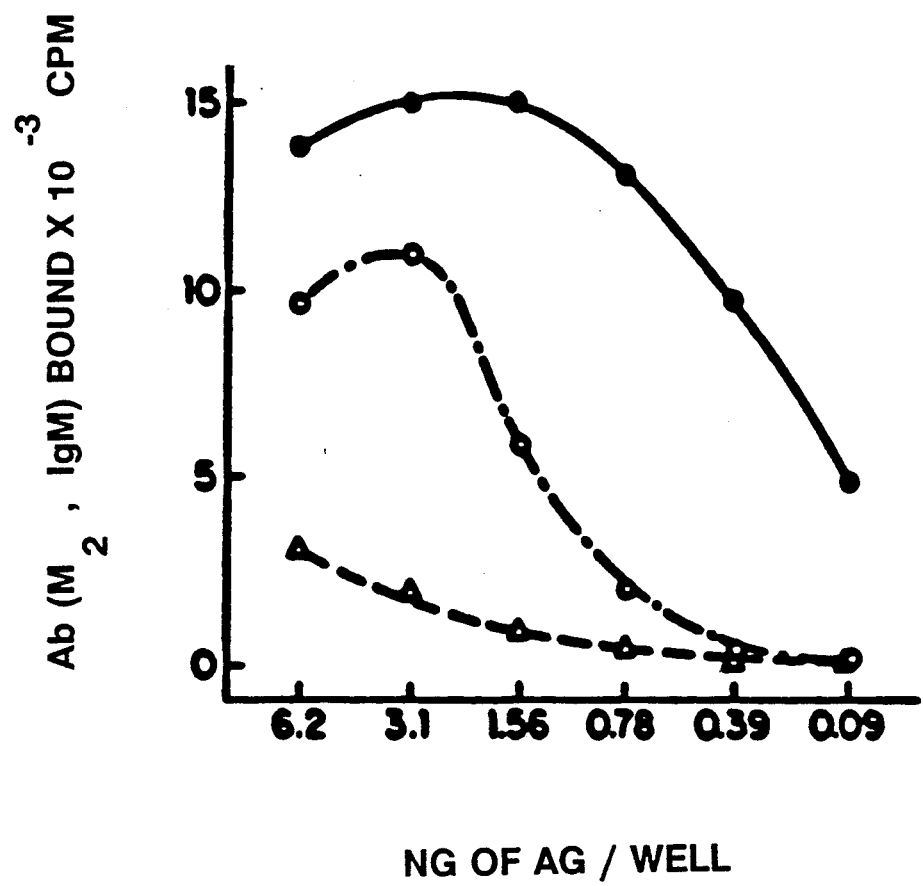
FIG. 6 shows reactivity of M2 using solid phase radioimmunoassay.

HT29-36 and CB showed reactivity with two major, one minor, and a few other faint bands in the total neutral glycolipid extracts of A and AB red cells using the immunostaining technique (FIG. 3). Glycolipids from B and O cells did not show reactivity. All samples showed a faint band corresponding to globoside; this was considered to be a non-specific reaction caused by the preponderance of globoside in these extracts. Using purified glycolipids it was shown that these two antibodies can react with A$^a$-1, A$^a$-2, A$^b$-2, and A$^a$-3 determinants (FIG. 4). Based on this information and their migration rates, the 2 major A red cell glycolipids reacting with antibodies HT29-36 and CB (FIG. 3) can be identified as A$^a$-2 (upper band) and A$^b$-2 and A$^a$-3 (lower band).

CLH6 was unreactive with glycolipids extracted from A, AB, B, and O red cells using the standard autoradiogram exposure times (FIG. 3). With longer exposures CLH6 could be shown to react weakly with a component in A and AB cells migrating just slower than A$^a$-2 (FIG. 3, fourth panel); this position corresponds to the migration position of A$^a$-1. In fact, when CLH6 was reacted with the standard glycolipids it was found that only A$^a$-1 glycolipid was stained with this antibody (FIG. 4).

S12 reacted with only two components in glycolipids extracted from A and AB erythrocytes and did not react with O or B cell glycolipids (FIG. 3). Analysis with purified glycolipids showed that S12 reacted with A$^a$-2 and A$^b$-2 and weakly with A$^a$-1 (FIG. 4). S12 was unreactive with A$^a$-3 glycolipid. Based on these results it is apparent that S12 stains only A$^a$-2 and A$^b$-2 in red cell glycolipids and is unreactive with any other species in these extracts.

M2 identified numerous glycolipids in extracts of A and AB erythrocytes but not from B or O erythrocytes (FIG. 3). This antibody reacted strongly with type 3 chain A (A$^a$-3) but not with A$^a$-2, A$^b$-2, or A$^a$-1 in immunostaining of thin layer plates (FIG. 4); the band observed with the A$^b$-2 sample is probably due to reactivity with A$^a$-3 which is known to contaminate this sample.

TABLE II

| | Reactivity of antibodies with glycoproteins from ovarian cyst and hog gastric mucin. | | | | | |
|---|---|---|---|---|---|---|
| MoAb | A (MSS) | A (Sullivan) | A + H (Hog) | B (Beach) | Le$^a$ (N-1) | HLe$^b$ (Tighe) |
| HT 29-36 | 0.27$^a$ | 0.82 | 2.50 | 1000 | 1000 | 1000 |
| CB | 0.05 | 0.16 | 0.48 | 420 | 595 | 707 |
| CLH6 | 0.03 | 0.16 | 12.80 | 1000 | 1000 | 1000 |
| S12 | 2.50 | 2.50 | 9.80 | 1000 | 1000 | 1000 |
| M2 | 4.30$^b$ | 4.30$^b$ | 1000 | 1000 | 1000 | 1000 |

$^a$Amount of glycoprotein (ug) showing 50% of plateau reaction in ELISA.
$^b$Partial reaction
Dilutions of antibodies used were: HT29-36, 1:200 of ascites fluid;
CB-1:100 of ascites fluid;
CLH6-1:5 of supernatant culture fluid;
S12-1:5 of supernatant culture fluid;
M2-1:100 of ascites fluid.

TABLE I

| | Reactivity of antibodies with erythrocytes and with glycoproteins from saliva. | | | | | |
|---|---|---|---|---|---|---|
| | Erythrocytes$^a$ | | | Salivary glycoproteins$^b$ | | |
| MoAb | A and AB | B | O | A and AB | B | O |
| HT29-36 | All (32/32) | — | — | All (10/10) | — | — |
| CB | All (74/74) | — | — | All (10/10) | — | — |
| CLH6 | None (0/32) | — | — | All (9/10)$^c$ | — | — |
| S12 | Some (59/74)$^d$ | — | — | Some (4/10)$^e$ | — | — |
| M2 | All (74/74) | — | — | None (0/10) | — | — |

$^a$Hemagglutination tests.
$^b$ELISA (results for "secretors" only shown); see FIG. 2 for examples.
$^c$Except for one A$_2$ individual.
$^d$See footnote 2.
$^e$Weak reactivity (see FIG. 2).

TABLE III

| Summary of reactivity of antibodies with glycolipids as determined by immunostaining. | | | | | |
|---|---|---|---|---|---|
| Glycolipid | HT29-36 | CB | CHL6 | S12 | M2 |
| A$^a$-1 | ++ | ++ | ++ | + | — |
| A$^a$-2 | ++ | ++ | — | ++ | — |
| A$^a$-3 | ++ | ++ | — | — | ++ |

TABLE III-continued

Summary of reactivity of antibodies with glycolipids as determined by immunostaining.

| Glycolipid | HT29-36 | CB | CHL6 | S12 | M2 |
|---|---|---|---|---|---|
| $A^b$-2 | ++ | ++ | − | ++ | − |
| $H_1$-3 | n.d. | n.d. | n.d. | n.d. | + |
| $A^x$ | n.d. | n.d. | n.d. | n.d. | ++ |
| Forssman | − | − | − | − | − |

TABLE IV

Inhibition of monoclonal antibodies by oligosaccharides[a].

| Antibody[b] | Oligosaccharide | | | |
|---|---|---|---|---|
| | A-tetra[c] | A-penta | A-hexa | A-hepta |
| HT29-36 | 1.3[d] | 0.9 | 1.9 | 0.7 |
| CB | 5.8 | 4.0 | 6.1 | 2.2 |
| CLH6 | 14.1 | 42.6 | 0.2 | 1.0 |
| S12 | 3.0 | 12.2 | 10.7 | 24.3 |
| M2 | 52.6 | 42.6 | 34.5 | 24.3 |

[a]Determined by ELISA method as described supra.
[b]Abs (10 ul) were diluted as follows:
HT29-36 (1:80)
CB (1:75)
CLH6 (undiluted culture fluid)
S12 (1:200)
M2 (undiluted culture fluid)
[c]See FIG. 1 for structure of oligosaccharides.
[d]nmoles required for 50% inhibition.

Further experiments were then performed which show that $S_{12}$ preferentially agglutinates $A_1$ erythrocytes. This is accomplished on the basis of non-structural differences between $A_1$ and $A_2$ cells.

$A_1/A_2$ Typing of Erythrocytes

A-type erythrocytes (74 samples) were obtained from the Blood Bank of Memorial Hospital. They were classified into $A_1$ and $A_2$ types using the anti $A_1$ lectin from *D. biflorus*.

Hemagglutination Assays

Red cell agglutination was performed by both macroscopic and microscopic methods as described supra.

Pronase Treatment of Erythrocytes

Erythrocytes were washed three times with PBS (with Ca/Mg). To the cell pellet was added 10 volumes of Pronase solution (10 ug/ml) in PBS (with Ca/Mg). After incubation at 37° C. for 30 min., the erythrocytes were washed 3 times with PBS and used for the hemagglutination assays.

Antibody Binding Assays

For analyzing the binding of monoclonal antibodies to $A_1$ and $A_2$ erythrocytes, S12 and CB were purified from mouse ascites fluid using a synthetic A antigen affinity chromatography method. Ascites fluid containing monoclonal antibody (0.6–0.8 ml.) was applied to a column of Synsorb A immunoadsorbent (1.2 ml.) and the unbound material was reapplied to assure maximum binding. Unreactive proteins were then removed by washing with PBS. Bound antibodies were then eluted by ammonium hydroxide (1%) and the eluate was immediately neutralized with saturated $KH_2PO_4$. Fractions with high antibody activity were combined with $^{125}I$ using the chloramine T method of Hunter, et. al. The specific activity of the labeled proteins was in the range of 0.07–0.20 uCi/ug.

Binding assays were performed in microcentrifuge tubes as follows: fifty ul of serially diluted $^{125}I$-labeled antibody was added to 50 ul of erythrocyte suspension ($1 \times 10^8$ cells/ml) in PBS containing 0.1% EDTA. After incubation at room temperature for 30 min., with occasional shaking, the mixture was layered onto 300 ul of 5% BSA in PBS containing 0.1% EDTA, and centrifuged for 45 seconds in an Eppendorf Centrifuge. The supernatants were removed and the tubes inverted. The tips of the tubes containing the erythrocyte pellets were cut off and counted in a gammacounter. The supernatant solution was also counted to determine the unbound fraction. Nonspecific binding of labeled antibody to erythrocytes was estimated by determining the effect of adding 100 fold larger aliquots of unlabeled antibody to the reaction mixtures.

Immunostaining of Glycolipids on Thin Layer Plates

Glycolipids were separated on TLC plates and stained with rabbit anti-mouse IgG and $^{125}I$-labeled protein A as described supra.

Lectin-Staining of Glycolipids on this Layer Plates

Staining of glycolipids on TLC plates by *D. biflorus* lectin was performed by a procedure similar to that used for immunostaining. Briefly, TLC was performed on aluminum backed silica gel sheets in chloroform-methanol-water (60:35:8). After drying, the sheet was soaked in n-heptane saturated with polyisobutylmethacrylate and then in PBS containing 2% BSA and 0.1% NaN for 2–3 hrs. A solution of *D. biflorus* lectin (20 ug/ml) was then added to the sheets and incubaed for 2 hrs. at room temperature. After washing, rabbit anti-*D. biflorus* lectin was added to a dilution of 1:100, and incubated for 1.5 hr. After washing, $^{125}I$-labeled protein A solution ($1 \times 10^6$ cpm/ml) was added and incubated for 1 hr. The sheet was washed and dried, then exposed to an X-ray film.

Hemagglutination Assays

Three monoclonal antibodies were examined for their ability to agglutinate $A_1$ and $A_2$ erythrocytes. As shown in Table VI, HT29-36 and M2 reacted more strongly with $A_1$ than $A_2$ erythrocytes but showed definite agglutination with both samples. On the other hand, S12 agglutinated only $A_1$ erythrocytes (titer: 1:10,240), and did not react with $A_2$ cells even using undiluted ascites fluid.

For further analysis of S12, we typed the erythrocytes from 74 A blood group individuals with this antibody and compared the the results with those obtained by reactivity with an anti A typing serum, M2 and *D. biflorus* lectin (Table VII). S12 agglutinated erythrocytes form 59 individuals and did not react with the other 15. The erythrocytes from the 15 unreactive donors also failed to be agglutinated by *D. biflorus*, showing that they were from $A_2$ individuals. When the 15 erythrocyte samples which showed no reaction with *D. biflorus* and S12 were treated with Pronase, all 15 became agglutinable by these reagents, although the intensity of the reactions were not as strong as with $A_1$ cells (see FIG. 8 for an example).

Antibody Bonding Analysis

The binding of $^{125}I$-labeled S12 and CB to $A_1$ and $A_2$ erythrocytes was determined as described above. The data were analyzed by the Scatchard method (*Ann. N.Y. Acad. Sci.* 51:660 (1949)) using a computer program to determine the best fit for the non-linear curve using a least squares method modified from Feldman

Figure 9:
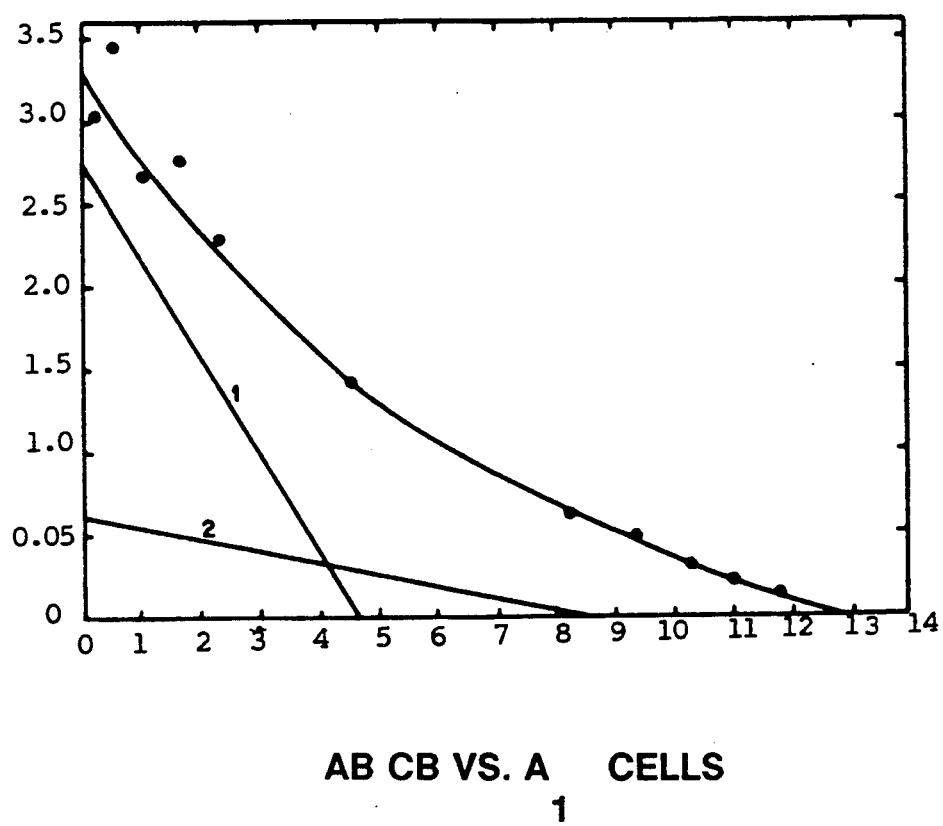
FIGS. 9A-9D compare binding of antibodies CB and S12 with A, and $A_2$ cells.
Figure 9:
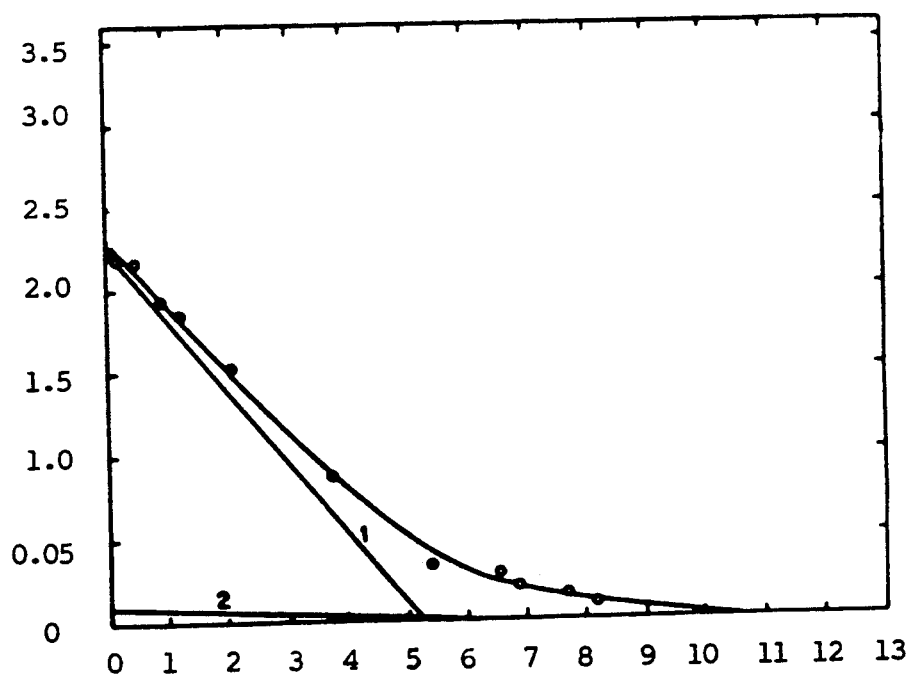
Figure 9:
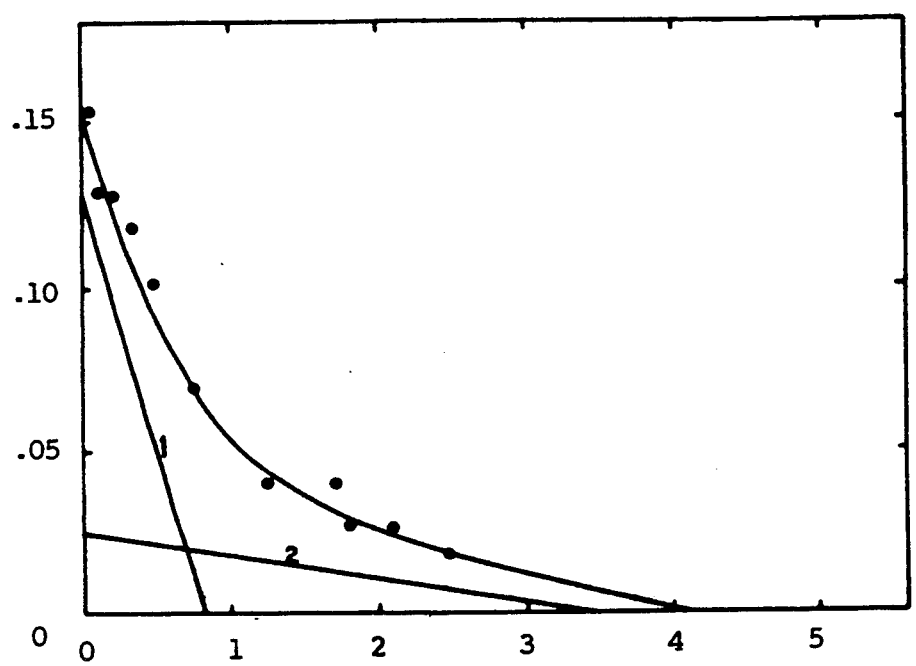
Figure 9:
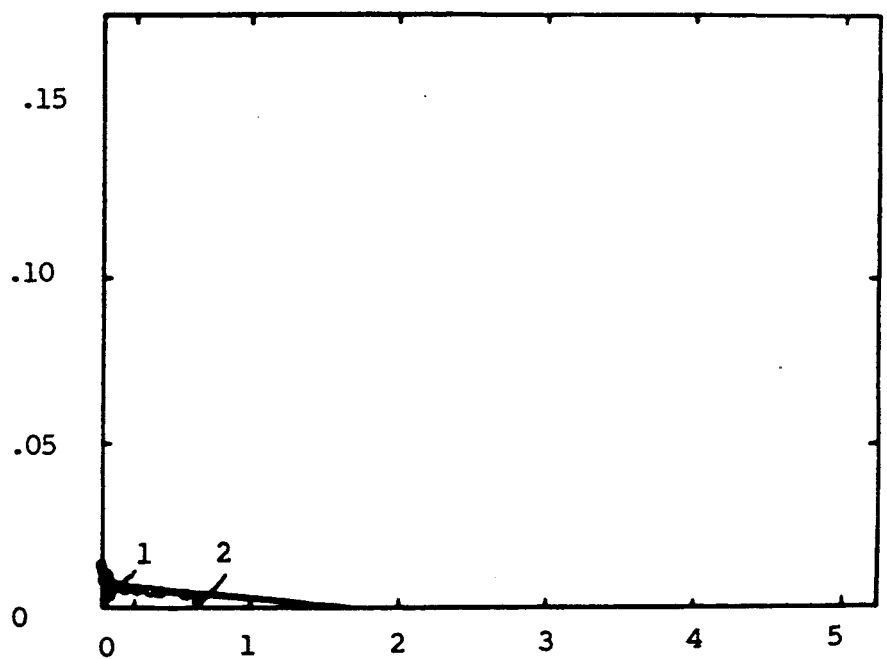

*Anal. Biochem.* 48:317 (1972). The data were best accommodated by a two-site model and curves were generated for high and low affinity interactions (1 and 2 in FIG. 9). From these data, apparent dissociation constants and the number of antibody-binding sites were calculated for the two antibodies against $A_1$ and $A_2$ cells (Table VIII). Antibody CB reacted with $5.6 \times 10^4$ and $6.3 \times 10^4$ high affinity sites and $10 \times 10^4$ and $6.7 \times 10^4$ low affinity sites on $A_1$ and $A_2$ erythrocytes, respectively. The total number of binding sites in $A_1$ cells is approximately the same as the value determined by Greenbury, et. al., *Immunol.* 6:421 (1963), using IgM anti-A but lower than the value obtained by these workers using IgG antibody. In contrast, S12 reacted with $1.0 \times 10^4$ high affinity sites on $A_1$ cells but with only $0.02 \times 10^4$ high affinity sites on $A_2$ cells. These results are consistent with the ability of S12 to agglutinate only $A_1$ erythrocytes.

Immunostaining of glycolipids with S12, CB and M2

Figure 10:
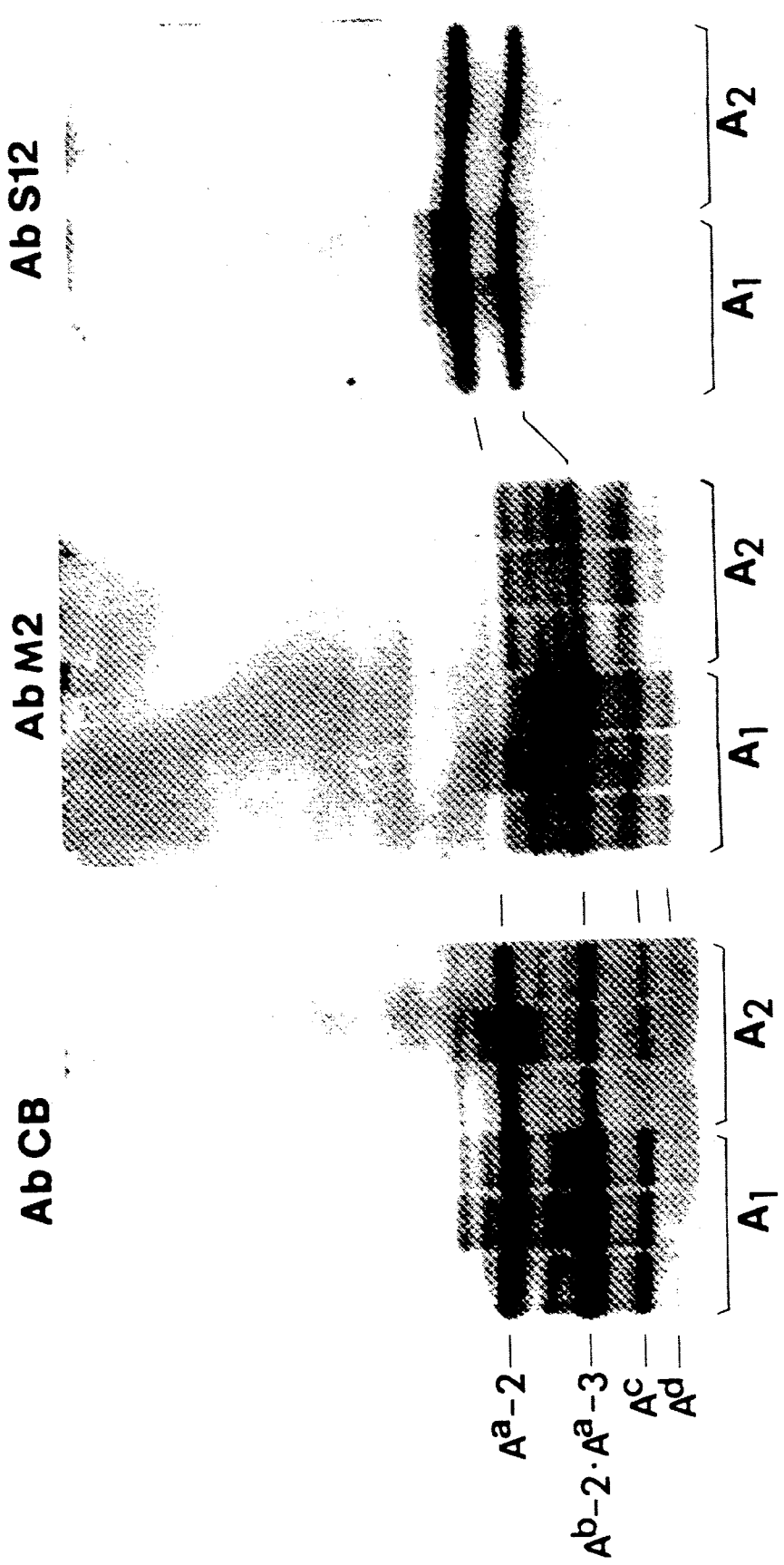
FIG. 10 shows CB, M2, and S12 binding, using immunostaining techniques.

In an attempt to elucidate the difference between $A_1$ and $A_2$ erythrocytes the neutral glycolipids extracted from 3 $A_1$ and 3 $A_2$ donors were immunostained with antibodies CB, S12 and M2 (FIG. 10). CB gave very similar staining patterns for the glycolipids from $A_1$ and $A_2$ cells, although the intensity was greater for $A_1$ cell glycolipids than for $A_2$ cell glycolipids. There were also a few qualitative differences between individual $A_2$ cell samples, for example, the red cells from one individual were deficient in $A^c$ glycolipid (FIG. 10 (Right), lane 4). M2, which detects type 3 A and H determinants, showed two characteristic differences between $A_1$ and $A_2$ cells (FIG. 10 (Center)). One difference was that a minor band migrating just below the type 2 $A^a$ position was stained more strongly in $A_2$ cells; the other was that the band migrating at the site of $A^c$ was consistantly split into 2 bands in $A_2$ cells. It should be emphasized, however, that these are relatively minor differences and, moreover, that M2 does not distinguish between $A_1$ and $A_2$ cells by agglutination. In contrast to these two antibodies, S12 stained only $A^a-2$ and $A^b-2$ glycolipids in both $A_1$ and $A_2$ cells, although again the intensity of staining was greater for $A_1$ cell glycolipids.

Lectin-Staining of Glycolipids

Figure 11:
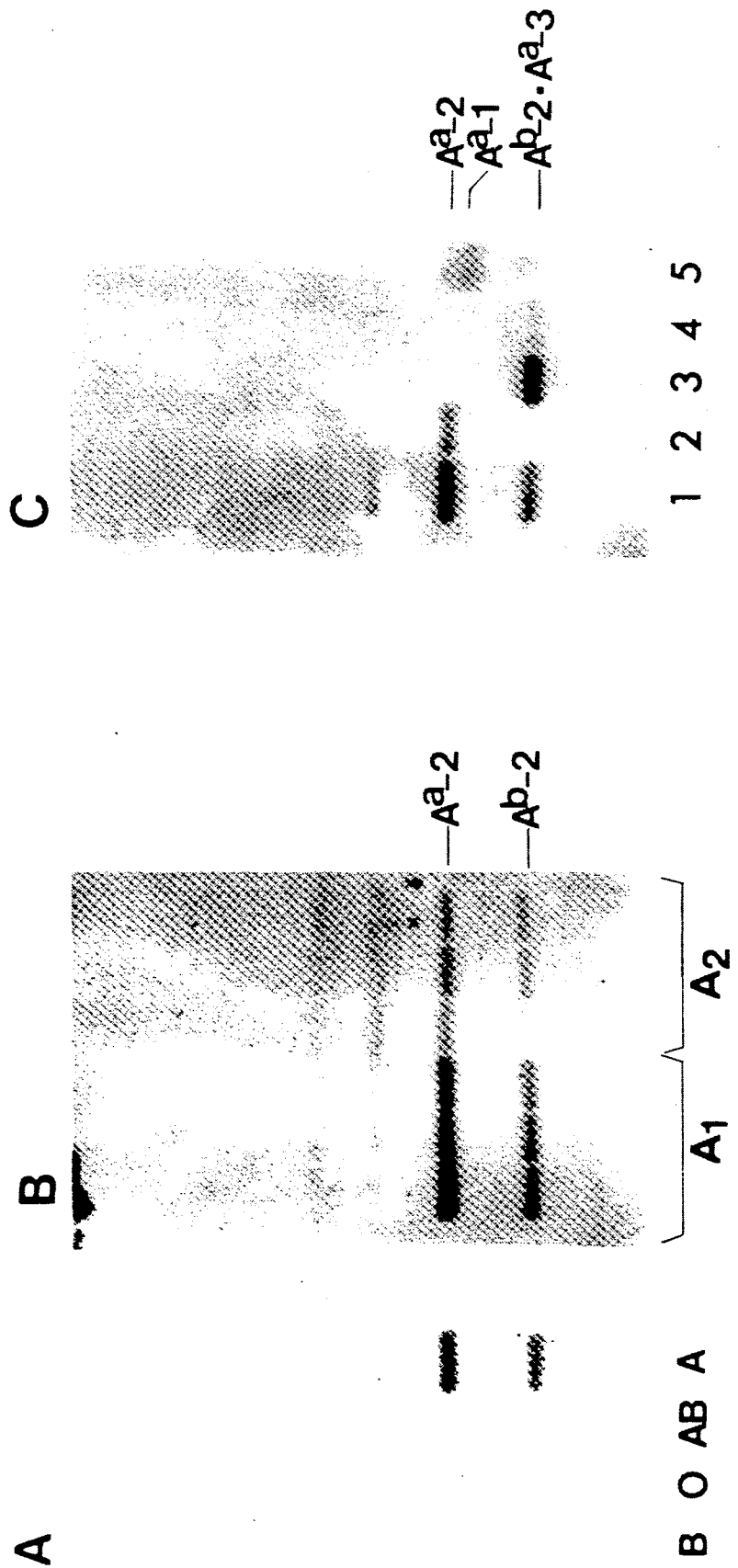
FIG. 11 illustrates determination of specificity of *D. biflorus* binding.

In order to elucidate the specificity of *D. biflorus* lectin the staining of 4 purified blood group A varient glycolipids were examined. $A^a-2$ and $A^b-2$ glycolipids were stained strongly and $A^a-1$ and $A^1-3$ showed weakly stained bands (FIG. 11C). These results were very similar to those obtained in the immunostaining of glycolipids by S12. When the neutral glycolipids from blood group B, O, AB, and A erythrocytes were examined, *D. biflorus* lectin stained two bands, corresponding to $A^a-2$ and $A^b-2$, in A and AB glycolipids (FIG. 11A). Neutral glycolipid fraction from 3 $A_1$ and 3 $A_2$ individuals were also examined. As shown in FIG. 11B, the lectin bound two components corresponding to $A^a-2$ and $A^b-2$ in both $A_1$ and $A_2$ extracts, with the intensity of $A_1$ bands being 4 times more intense than the staining of $A_2$ bands.

TABLE V

Reactivity of three monoclonal anti-A antibodies and *D. biflorus* lectin with $A_1$ and $A_2$ erythrocytes.

| Reagent[1] | Hemagglutination titer[2] | |
|---|---|---|
| | $A_1$ | $A_2$ |
| HT29-36 | 2,560 | 1,280 |
| M2 | 5,120 | 1,280 |
| S12 | 10,240 | 0 |
| *D. biflorus* lectin | 450 | 0 |

[1]Ascites or nu/nu serum form of antibodies was used. The initial concentration of lectin was 2 mg/ml.
[2]Highest dilution giving 1+ agglutination.

TABLE VII

Summary of hemagglutination assays with 74 type A blood samples.

| | Anti-A typing serum | Agglutination | | | | | |
|---|---|---|---|---|---|---|---|
| | | S12 | | M2 | | *D. biflorus* | |
| Erythrocytes | | U[2] | P[3] | U | P | U | P |
| 59 samples | ++ | ++ | ++ | ++ | ++ | ++ | ++ |
| 15 samples | ++ | − | + | + | + | − | + |

Figure 8:
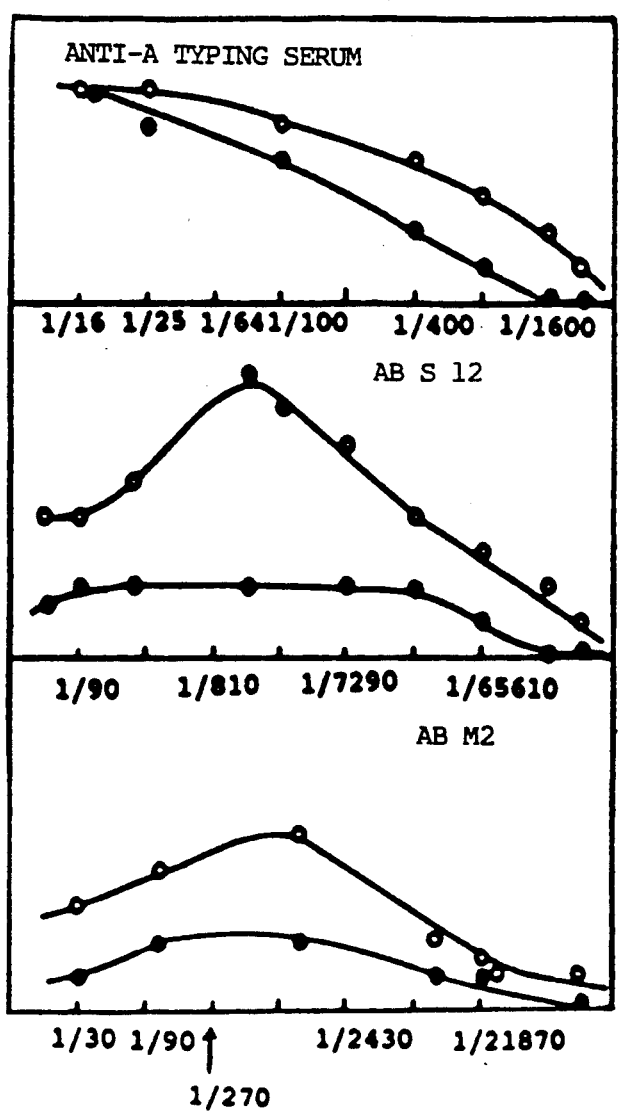
FIGS. 8A and 8B show reactivity of erythrocytes with anti-A typing serum, S12, and M2, both before and after treatment with pronase.

[1]-See FIG. 8 for examples of these results.
[2]Untreated.
[3]Pronase treated.

Monoclonal antibodies CB and HT29-36 were derived quite differently but nevertheless showed very similar serological specificity. They both could agglutinate all A and AB erythrocytes tested and reacted, without exception, with all A and AB salivas. In TLC immunostaining they reacted with all blood group A variant structures examined including $A^a-1$, $A^a-2$, $A^b-2$ and $A^a-3$. In inhibition assays with oligosaccharides they were inhibited by type 1 and type 2 as well as by mono- and di-fucosyl structures. These results imply that the determinant structure detected by these antibodies was the determinant which is common to all A variants:

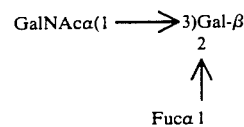

In addition to the 2 main erythrocyte glycolipids (type 2 $A^a$ and type 2 $A^b$), these two antibodies also stained bands migrating between $A^a-2$ and $A^b-2$ on TLC plates. One more band was detected which migrated below $A^b-2$ and probably corresponds to $A^c$ and a fainter band moving at a position corresponding to $A^d$ (Hakomori, *Semin. Hematol.* 18:39-62 (1981)) was observed.

CLH6 reacted strongly only with glycolipids and oligosaccharides containing type 1 A determinants, namely:

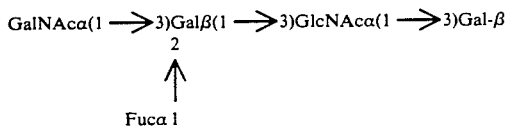

This antibody did not react with type 2 or type 3 determinants. These results suggest that CLH6 has the same, or very similar specificity as H21 previously reported by Abe, et. al., supra. It is interesting to note that although CLH6 does not agglutinate red cells and reactivity with red cell glycolipids could normally not be detected, longer exposure of the autoradiograms revealed a component migrating with type 1 $A^a$. This result indicates that although the main glycolipids of red cells are of type 2 and type 3, a small amount of type 1 blood group glycolipids may also be present; these species are probably absorbed from serum in the same way that $Le^a$ and $Le^b$ are acquired by red cells (see, e.g., Marcus and Cass, (1969).

In contrast to the other antibodies S12 reacted with only a proportion of red cell samples and salivas from A and AB individuals. In immunostaining experiments, S12 was shown to react only with $A^a-2$ and $A^b-2$ (and weakly with $A^a-1$); it did not recognize any of the longer chain A structures in red cells even on long exposure of the X-ray film. S12 was inhibited best by the A-tetra oligosaccharide. These results indicate that S12 is specific for short, unbranched, type 2 monofucosyl A determinants. The poor reactivity of S12 with A saliva in comparison to ovarian cyst glycoproteins is consistent with the earlier report that salivary glycoproteins are richer in difucosyl than in monofucosyl structures (Sakamoto, et. al., *Mol. Immunol.* 21:1093-1098 (1984)); the reason why only 4/10 salivas were reactive is unclear.

Figure 7:
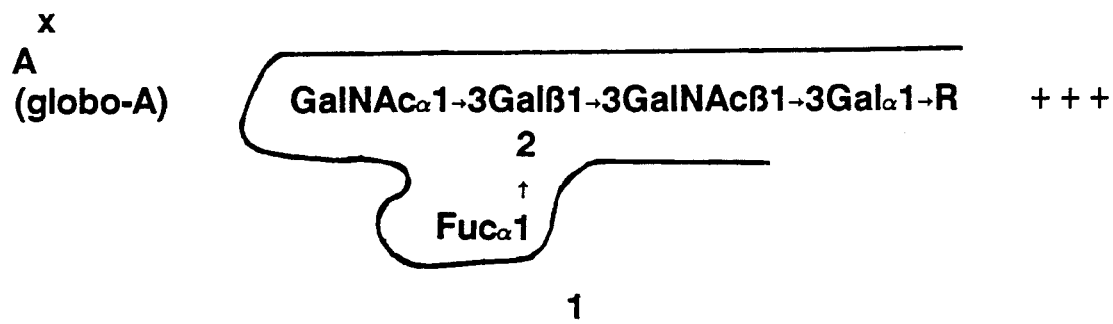
FIGS. 7A and 7B show the derivation of the reaction site (determinant) for M2.
Figure 7:
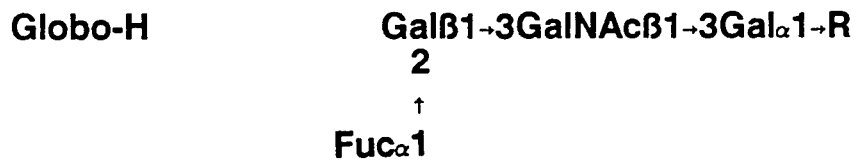
Figure 7:
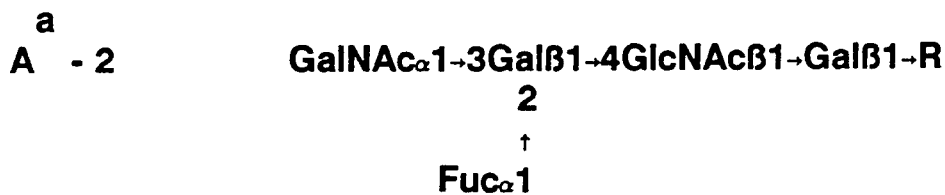

M2 agglutinated A and AB erythrocytes but did not react type $2-A^a$ and $-A^b$ glycolipids or with type 1 or type 2 mono- anddifucosyl A oligosaccharides. Among 8 blood group A variant structures examined, M2 could react with only type 3 glycolipids ($A^a-3$ and $H_1-3$) and with type 4 A ($A^x$) glycolipid. With whole erythrocyte glycolipids M2 also reacts with components migrating at the positions of $A^c$ and $A^d$; this result suggests that there may be other red cell glycolipids having type 3 or type 4 structures which have not yet been identified. From these results it is concluded that M2 has a complex specificity. It appears to have a large combining site, comprising two subsites, one recognizing external and the other recognizing internal structures (FIG. 7). Since M2 reacts with both $A^a-3$ and $A^x$(globo-A), but not (or very weakly) with $A^a-1$ and $A^a-2$, it is clear that it is reactive with the terminal A structure (subsite 1 in FIG. 7). Since it also reacts with the $H_1-3$ structure and weakly with Gal-$A^a$ the binding site must also encompass the internal A sequence (subsite 2 in FIG. 7). The relatively strong binding to $H_1-3$ in comparison to Gal-$A^a$ can be explained by the presence of the additional L-fucose residue in $H_1-3$ which contributes to the interaction through subsite 1. The results show that unlike previously described anti-A antibodies M2 has a strong preference for binding type 3 and type 4 chains over type 1 and type 2 chains.

Unexpectedly, M2, even though it agglutinated all A erythrocytes, did not react with any of the A or AB salivas tested in the ELISA assay. In contrast, HT29-36, CB and CLH6 reacted with all A and AB salivas. That the non-reactivity of M2 is due to a characteristic of the A determinants in saliva was shown by the fact that M2 was able to react with human ovarian cyst fluid A glycoproteins. A probable explanation for these results is that A saliva mucins have type 1 and type 2 sequences (which are recognized by CB, HT29-36 and CLH6), but lack type 3 and type 4 sequences (which would be recognized by M2).

These monoclonal antibodies (except for CB) were generated by immunization of mice with various human cancer cell lines. The fact that these antibodies react with different determinants belonging to the blood group A family suggests the possibility that cancer cells may express a variety of A antigenic determinants on their surfaces which cannot be distinguished by conventional reagents. With the availability of a panel of well-characterized anti-A blood group reagents it will be possible to analyze the expression of A antigen variants in normal tissues and in tumor samples to search for alterations of expression in malignancy.

The fine specificity of antibody S12 and *Dolichos biflorus* lectin, the two reagents capable of distinguishing $A_1$ from $A_2$ erythrocytes, resemble each other quite closely and differ significantly from the other anti-A reagents studied. As demonstrated supra, S12 reacts best with short chain, unbranched, type 2 determinants and as shown in this study, *D. biflorus* lectin also reacts optimally with the same structures in glycolipids. The latter result is in agreement with the conclusions of other workers using oligosaccharides and sugars. Thus, Etzler and Kabat, *Biochemistry* 9:869 (1970) showed that an A-active type 2 pentasaccharide was only twice as effective an inhibitor as methyl 2-acetamido-2-deoxy--D-galactoside.

In terms of their reactivity with erythrocyte glycolipids, both S12 and *D. biflorus* lectin reacted almost exclusively with only two species $-A^a-2$ and $A^b-2$ whereas HT29-36 and M2 detected multiple species (FIGS. 3 and 4). Although S12 and *D. biflorus* lectin detected only $A^a-2$ and $A^b-2$ in both $A_1$ and $A_2$ erythrocyte glycolipids, there was a quantitative difference in the amount of these glycolipids in the two cell types with $A_1$ cells expressing approximately 4 times more of these species than $A_2$ cells as estimated in the immunostaining experiments. It is possible that S12 could react with determinants on glycoproteins also, however, such reactivity could not be detected in Western blotting experiments.

These results show that S12 and *D. biflorus* lectin can distinguish between $A_1$ and $A_2$ erythrocytes even though they detect structures present in both cell types. The mechanism by which they do so is not so clear. Binding studies showed that S12 reacts with sets of both high and low affinity sites in $A_1$ cells whereas only low affinity sites are detected on $A_2$ cells, strongly suggesting that high affinity sites are required for agglutination. The ability of S12 and the lectin to preferentially bind to $A_1$ cells could be explained by (i) differences in quantitative levels of the type 2 A determinants such that the density of determinants may not be sufficient for multiple binding to $A_2$ cells, (ii) differences in the ability of the epitopes to aggregate on the cell surface, which could influence binding, (iii) the inaccessibility to antibody of short chain A structures in $A_2$ cells because of steric hindrance by other cell surface components, or (iv) combinations of these factors. The ability of S12 to agglutinate Pronase-treated $A_2$ (albeit weakly) supports the importance of the exposure of the antigenic determinants. Williams and Voak, *Brit. J. Haematol*, 23:427 (1972), showed that papain treatment has a similar effect on agglutination of $A_2$ cells by *D. biflorus* lectin.

The basis for the characteristics and ability of anti-A antibodies and lectins which allow some of them to distinguish between $A_1$ and $A_2$ cells for clearly varies between different reagents. It has been suggested in, e.g., Greenburg, supra, that low affinity IgM antibodies must form multivalent interactions to cause agglutination and that $A_1$ cells have a sufficient density of sites to allow multivalent binding whereas $A_2$ cells do not. Certainly S12 has a lower effective binding affinity for red cells than CB, even though they are both IgM antibodies, in agreement with this observation. Nevertheless, it is also true that antibodies which cause agglutination of $A_2$ cells (such as CB) react with a greater spectrum of cell surface glycolipids, including more complex glycolipids, than do those (such as S12) which do not (FIG. 3). The failure of S12 to react with branched and complex glycolipids suggests that its binding site includes the terminal five sugars of $A^a$ and $A^b$ structures. One possible interpretation of the binding data is that high affinity binding to $A_2$ cells requires recognition of both branched and simple A chains, while in $A_1$ cells recognition of unbranched A chains is sufficient for high affinity binding.

It is interesting to compare S12 with the anti-$A_1$-specific antibody (TH1) recently described by Clausen, et. al., PNAS, 82:1199 (1985). This antibody reacts with a repetitive A epitope (type 3 A chain) and distinguishes between $A_1$ and $A_2$ cells on the basis of the preferential expression of type 3 A glycolipids in $A_1$ erythrocytes. Thus, this reagent contrasts strongly with S12 and *D. biflorus* lectin which do not recognize qualitative differences between the two cell types. Other antibodies such as CB, HT29-36 and M2, which have broader specificities and detect multiple erythrocyte glycolipids, are not capable of providing a clear-cut distinction between $A_1$ and $A_2$ erythrocytes. In fact, M2 also reacts with type 3 A determinants but in contract to TH1, it also reacts with type 3 H determinants. Since this structure is also found on A cells, M2 is able to agglutinate $A_2$ as well as $A_1$ cells. It can be concluded, therefore, that both views of $A_1/A_2$ (qualitative vs. quantitative differences) are correct depending on the properties of the reagent being used to distinguish between the two cell types. A more basic question concerns the underlying basis for the difference between $A_1$ and $A_2$. Two distinct possibilities are: (i) the $A_1$ N-acetylgalactosaminyl transferase has a different structure resulting in a broader specificity or (ii) a regulatory protein or sequence affects the level of a single transferase such that $A_1$ cells have higher levels of all A species, including type 3 and type 4 chains as well as $A^a$ and $A^b$ structures.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A panel useful in determining the presence of different forms of type A blood group antigen, said panel comprising at least one antibody selected from the group consisting of HT29-36 (ATCC HB 8875), M2 (ATCC HB 8346), S12 (ATCC HB 8875), and CLH6 (ATCC HB 8232), and wherein at least one antibody is S12 (ATCC HB 8875).

2. A method of determining different forms of type A blood group antigen in a sample, comprising contacting a sample known to contain said antigen with the panel of claim 22 with specificity for different forms of said antigen under conditions favoring formation of antigen-antibody complexes between said antigen and the panel and observing formation of said complexes.

3. A method as in claim 2, wherein said sample comprises a cell sample.

4. A method as in claim 2, wherein said sample comprises a tissue sample.

5. A method as in claim 2, wherein said sample comprises cancerous material.

6. A method as in claim 5, wherein said cancerous material is carcinogenic tissue.

7. A method as in claim 5, wherein said cancerous material is cancer cells.

* * * * *